United States Patent [19]
Goodbrand et al.

[11] Patent Number: 5,902,901
[45] Date of Patent: *May 11, 1999

[54] ARYLAMINE PROCESSES

[75] Inventors: H. Bruce Goodbrand, Hamilton; George Liebermann, Mississauga; Roger E. Gaynor, Oakville, all of Canada

[73] Assignee: Xerox Corporation, Stamford, Conn.

[*] Notice: This patent is subject to a terminal disclaimer.

[21] Appl. No.: 09/074,620

[22] Filed: May 7, 1998

[51] Int. Cl.$^6$ .................................................. C07C 209/10
[52] U.S. Cl. ........................ 564/405; 564/307; 564/395; 564/433; 564/435
[58] Field of Search .................................... 564/405, 433, 564/307, 395, 435

[56] References Cited

U.S. PATENT DOCUMENTS

| | | | |
|---|---|---|---|
| 3,121,006 | 2/1964 | Middleton et al. | 96/1 |
| 4,240,987 | 12/1980 | Martin et al. | 570/206 |
| 4,265,990 | 5/1981 | Stolka et al. | 430/59 |
| 4,298,697 | 11/1981 | Baczek et al. | 521/27 |
| 4,299,983 | 11/1981 | Martin et al. | 564/394 |
| 4,338,390 | 7/1982 | Lu | 430/106 |
| 4,485,260 | 11/1984 | Szabo et al. | 564/402 |
| 4,560,635 | 12/1985 | Hoffend et al. | 430/106.6 |
| 4,563,408 | 1/1986 | Lin et al. | 430/159 |
| 4,584,253 | 4/1986 | Lin et al. | 430/59 |
| 4,585,804 | 4/1986 | Lancaster et al. | 521/128 |
| 4,764,625 | 8/1988 | Turner et al. | 548/442 |
| 5,648,539 | 7/1997 | Goodbrand | 564/309 |
| 5,648,542 | 7/1997 | Goodbrand et al. | 564/405 |
| 5,654,482 | 8/1997 | Goodbrand | 564/405 |
| 5,705,697 | 1/1998 | Goodbrand et al. | 564/405 |
| 5,723,669 | 3/1998 | Goodbrand et al. | 564/307 |
| 5,723,671 | 3/1998 | Goodbrand et al. | 564/405 |

*Primary Examiner*—Brian M. Burn
*Attorney, Agent, or Firm*—E. O. Palazzo

[57] ABSTRACT

A process for the preparation of N,N-bis(3,4-dimethylphenyl)-4-biphenylamine which comprises the reaction of N,N-bis(3,4-dimethylphenyl)amine and an iodobiphenyl in the presence of a ligand copper catalyst, and wherein the ligand is selected from the group consisting of monodentate tertiary amines and bidentate tertiary amines, and which reaction is accomplished at a temperature of, for example, from about 120° C. to about 150° C.

27 Claims, No Drawings

ARYLAMINE PROCESSES

Disclosed in U.S. Pat. No. 5,648,542, U.S. Pat. No. 5,654,482, and U.S. Pat. No. 5,648,539, the disclosures of each patent being totally incorporated herein by reference, are generally processes for the preparation of arylamines. For example, in U.S. Pat. No. 5,648,542 and U.S. Pat. No. 5,654,482, respectively, there is disclosed a process for the preparation of triarylamines which comprises the reaction of an aniline and a haloaromatic component in the presence of a ligated copper catalyst, and wherein the ligand is selected from the group consisting of monodentate tertiary amines and bidentate tertiary amines, and which reaction is accomplished at a temperature of, for example, from about 120° C. to about 150° C., and an Ullmann condensation process for the preparation of triarylamines which comprises the reaction of an aniline and a halobenzene in the presence of an organic solvent, an alkali metal hydroxide, a ligated copper catalyst and wherein the ligand is selected from the group consisting of monodentate tertiary amines and bidentate tertiary amines, and which reaction is accomplished at, for example, a temperature of from about 120 to about 135° C.

Moreover, in U.S. Pat. No. 5,723,669, U.S. Pat. No. 5,705,697, and U.S. Pat. No. 5,723,671, the disclosures being totally incorporated herein by reference, there are illustrated arylamine processes, and more specifically, a process for the preparation of N,N-bis(3,4-dimethylphenyl)-4-biphenylamine which comprises the reaction of N-(3,4-dimethylphenyl)4-biphenylamine and an iodoxylene in the presence of a ligated copper catalyst, and wherein the ligand is selected from the group consisting of monodentate tertiary amines and bidentate tertiary amines, and which reaction is accomplished at a temperature of, for example, from about 120° C. to about 150° C.; and a process for the preparation of N,N-bis(3,4- dimethylphenyl)-4-biphenylamine which comprises the reaction of an aminobiphenyl and an iodoxylene in the presence of a ligand copper catalyst, and wherein the ligand is selected from the group consisting of monodentate tertiary amines and bidentate tertiary amines, and which reaction is accomplished at a temperature of from about 120° C. to about 150° C.

BACKGROUND OF THE INVENTION

This invention is generally directed to processes for the preparation of arylamines, useful for photoconductive imaging members, and more specifically, the present invention relates to the preparation of N,N- bis(3,4-dimethylphenyl)-4-biphenylamine. In embodiments, the present invention relates to an improved process for the preparation of hole transporting molecules, such as arylamines, and wherein there are selected certain copper (II) catalysts, and in embodiments low temperatures, for example about 105° C. The catalysts selected for the processes of the present invention include ligated copper salts, and more specifically, copper (II) salts, and wherein the ligands are characterized as monodentate tertiary amines and bidentate tertiary amines, such as 1,10-phenanthroline, or pyridine, and the like. The products obtained, such as N,N-bis(3,4-dimethylphenyl)-4-biphenylamine, with the processes of the present invention can be incorporated as hole transport molecules into layered photoconductive imaging members with a photogenerating layer, a charge transport layer, and a supporting substrate, reference for example U.S. Pat. No. 4,265,990, the disclosure of which is totally incorporated herein by reference. The aforementioned layered photoconductive imaging members can be negatively charged when the photogenerating layer is situated between the charge transport layer and the substrate, or positively charged when the charge transport layer is situated between the photogenerating layer and the supporting substrate. The layered photoconductive imaging members can be selected for a number of different known imaging and printing processes including, for example, electrophotographic imaging processes, especially xerographic imaging and printing processes wherein negatively charged or positively charged images are rendered visible with toner compositions of the appropriate charge, and for digital processes. Generally, the imaging members are sensitive in the wavelength regions of from about 500 to about 850 nanometers, thus diode lasers can be selected as the light source.

PRIOR ART

Processes for the preparation of certain charge transporting molecules are known, reference for example U.S. Pat. Nos. 4,485,260; 4,240,987; 4,764,625 and 4,299,983, the disclosures of each of these patents being totally incorporated herein by reference. These and other prior art illustrate the Ullmann condensation of 3-methyidiphenylamine and diiodobiphenyl at high temperatures, for example 160° C., reference the U.S. Pat. No. 4,764,625 patent, and wherein certain copper catalysts, such as cupric oxide catalysts are selected. With these processes, the crude charge transport molecules generated are of lower quality and possess lower purity than the charge transport molecules obtained with the processes of the present invention. Higher crude purities enable a much wider choice of purification protocols. Generally, high temperature reactions are more prone to produce troublesome impurities necessitating extensive purification. This becomes particularly important when products with electronic grade purities are required, such as for use as charge transporting molecules in layered photoconductive xerographic imaging members, reference U.S. Pat. No. 4,265,990, the disclosure of which is totally incorporated herein by reference. Moreover, lower temperatures have a positive influence on the economics of these processes primarily because of reduced energy demands.

European Patent Publication EP 0 617 005 A2 discloses certain aryl amines, and more specifically, triacrylamines of Formula (I), which can be prepared by acetylating 3,4-xylidene, thereafter condensing the acetylated product with a halogenated aryl compound to form N-(3,4-dimethylphenyl)-N-arylamine, and then condensing the diarylamine compound with a certain halogenated aryl compound of the formula $Ar_2X$, see for example page 4 of this patent publication, and wherein a certain copper catalyst of a metallic copper powder, copper sulfate, cupric oxide, copper iodide, copper nitrate, are selected, see page 4, beginning at line 46. This publication also indicates that the condensation temperature is high, 200° C., and the reaction can consume substantial time, for example 30 hours. Long reaction times at high temperature are apparently required for the above patent publication process to secure the desired product. In contrast with the present invention, there is provided in embodiments thereof a process for the preparation of bis(3,4-dimethylphenyl)-4-biphenylamine under substantially milder conditions from commercially available raw materials, and wherein ligated catalysts are selected, which catalysts are not believed to be illustrated in the patent publication. Furthermore, with the present invention in embodiments there is provided with the copper ligand catalysts selected shorter reaction times for the synthesis of the amine product, and wherein the desired product is of high purity, for example 95 percent pure, and which product can be easily further purified to an electronic grade of about 99.7 percent pure or greater.

Other prior art that may be of interest includes Japanese Patent Publications 93-851153, 93-136927, and 93-191821.

SUMMARY OF THE INVENTION

Examples of features of the present invention include in embodiments of the following.

It is a feature of the present invention to provide processes for the preparation of charge transport arylamines with many of the advantages illustrated herein, and wherein the charge transporting, especially hole transporting components resulting, can be selected for layered photoconductive imaging members.

It is yet another feature of the present invention to provide low temperature processes for the preparation of charge transport components, especially N,N-bis(3,4-dimethylphenyl)-4-biphenylamine.

Another feature of the present invention resides in the preparation of charge transport components by the Ullmann condensation reaction, and wherein organic ligands of copper (II) are selected as catalyst adjuvants, or catalyst accelerators.

Further, in another feature of the present invention there are provided economically scaleable processes for the preparation of arylamines, especially N,N-bis(3,4-dimethylphenyl)-4-biphenylamine, quickly and in high purity and in excellent yields.

Another feature of the present invention relates to processes wherein there can be selected low temperatures of, for example, from about 100°C. to about 150° C., and preferably from about 120° C. to about 130° C., and wherein organic ligands of copper are selected as a catalyst accelerator, and wherein the crude product obtained is of excellent purity, and which product may be further purified by known methods, such as filtration, distillation, column chromatography, vacuum distillation, and the like.

A further specific feature of the present invention resides in the provision of photoresponsive imaging members with an arylamine hole transport layer, especially a hole transport layer comprised of N,N-bis(3,4- dimethylphenyl)-4-biphenylamine obtained by the processes illustrated herein, and a photogenerator layer.

Moreover, in another feature of the present invention there are provided processes for the scaleable preparation of hole transporting molecules wherein the temperature of the reaction can be lower than the about 160° C. to about 220° C. presently utilized for the preparation of certain commercial hole transporting arylamines, and more specifically, wherein the invention reaction in embodiments can be accomplished, for example, at temperatures 80° lower than 200° C., and yet more specifically, at about 100C. to about 110° C.; and also wherein novel catalysts, such as the product of cupric acetate monohydrate, and a 1,10-phenanthroline chelating agent are selected as a catalyst. The aforementioned lower temperature, milder reaction conditions and shorter reaction times enable, it is believed, simpler processes, and more efficient protocols for the preparation of pure, that is, for example, electronic grade, arylamines.

Moreover, another feature of the present invention resides in the avoidance of highly corrosive, for example corrosive to steel halide counterions by utilizing the more benign acetate counterion, and which is not believed to be the situation with copper (I) salt catalyst since, for example, copper (I) acetate is not considered a stable chemical entity. Additionally, copper (II) salts are advantaged, it is believed, both in respects of stability and cost as compared to the corresponding copper (I) salt catalysts.

Further, in another feature of the present invention in embodiments thereof there may be enabled, it is believed, processes for the preparation of oligomers, polymers, intermediates, and the like.

Aspects of the present invention relate to a process for the preparation of N,N-bis(3,4-dimethylphenyl)-4-biphenylamine which comprises the reaction of N,N-bis(3,4-dimethylphenyl)amine and an iodobiphenyl in the presence of a ligand copper catalyst, wherein copper is of a valence of two and wherein the ligand is selected from the group consisting of monodentate tertiary amines and bidentate tertiary amines; a process wherein the reaction is accomplished by heating; a process wherein subsequent to heating, cooling is accomplished, and the N,N-bis(3,4-dimethylphenyl)-4-biphenylamine product is isolated, and wherein the iodobiphenyl is 4-iodobiphenyl; a process wherein the temperature is from about 100° C. to about 150° C.; a process wherein the temperature is about 105° C. to about 150° C.; a process wherein from about 0.01 to about 0.1 molar equivalents of the ligated copper catalyst are selected, the amount of bis(3,4-dimethylphenyl)amine selected is from about 0.95 to about 1.1 molar equivalents, and the amount of iodobiphenyl selected is about 1 molar equivalent; a process wherein the reaction is accomplished in the presence of a hydrocarbon solvent of toluene or xylene; a process wherein the copper is copper (II); a process wherein said ligand is selected from the group consisting of 1,10-phenanthrolinepyridine and pyridine; a process wherein the N,N-bis(3,4-dimethylphenyl)amine is of the formula

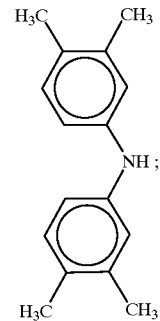

process wherein the N,N-bis(3,4-dimethylphenyl)-4-biphenylamine product is of the formula

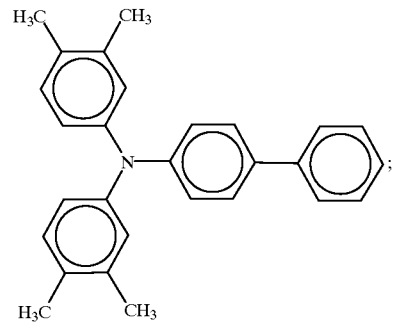

a process wherein the iodobiphenyl is of the formula

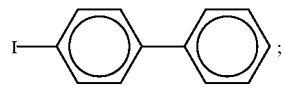

a process wherein subsequent to heating, cooling is accomplished, and the N,N-bis(3,4-dimethylphenyl)-4-biphenylamine product is isolated; a process for the preparation of N,N-bis(3,4-dimethylphenyl)-4-biphenylamine which comprises the reaction of bis(3,4-dimethylphenyl) amine and 4-iodobiphenyl in the presence of a ligand copper (II) catalyst, and wherein the ligand is selected from the group consisting of monodentate tertiary amines and bidentate tertiary amines, and which reaction is accomplished at a temperature of from about 120° C. to about 150° C., followed by cooling and isolating the N,N-bis(3,4-dimethylphenyl)-4-biphenylamine product; a process wherein the temperature is from about 120° C. to about 130° C.; a process wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate; a process wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate or dipyridino copper (II) acetate; a process wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate or dipyridino copper (II) acetate; a process wherein said catalyst is represented alternatively as follows

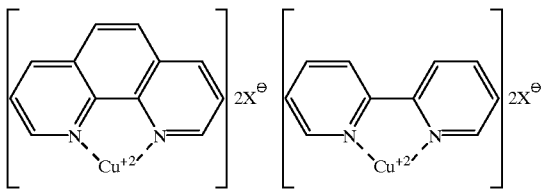

wherein X is suitable substituent, such as preferably a halide or acetate; a process wherein said catalyst is of the alternative formulas

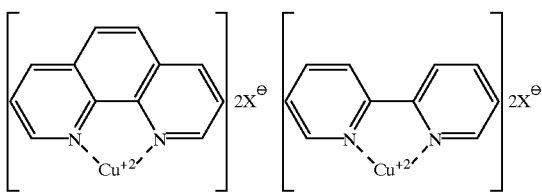

wherein X is a halide or acetate; a process wherein said catalyst is of the alternative formulas

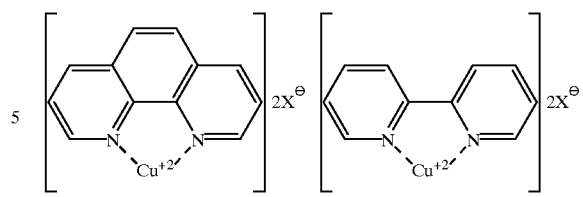

wherein X is a halide or acetate; a process wherein X is acetate; a process wherein X is chloride; a process for the preparation of an arylamine which comprises the reaction of an arylamine and an iodobiphenyl in the presence of a ligand copper (II) catalyst; a process wherein said catalyst is of the alternative formulas

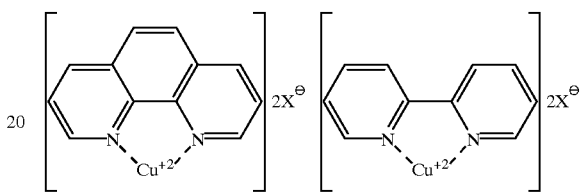

wherein X is an acetate, or halide; a process wherein heating is accomplished at about 105° C.; a copper ligand catalyst; a catalyst of the alternative formulas

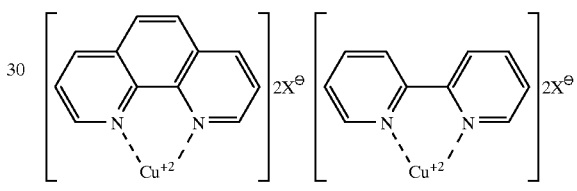

wherein X is as illustrated herein, and processes for the preparation of arylamines, and more specifically, processes for the preparation of N,N-bis(3,4-dimethylphenyl)-4-biphenylamines, and which amines can be selected as charge transport molecules in layered photoconductive imaging members, reference U.S. Pat. Nos. 4,265,990; 4,585,804; 4,584,253; 4,563,408 and 4,764,625, the disclosures of which are totally incorporated herein by reference; the reaction of an appropriate amine, such as bis(3,4-dimethylphenyl)amine with an iodobiphenyl, especially 4-iodobiphenyl in the presence of a ligated copper II catalyst, and wherein the ligand is selected from the group consisting of monodentate tertiary amines and bidentate tertiary amines; the appropriate amine, such as N,N-bis(3,4-dimethylphenyl)amine, can be obtained from a number of chemical companies, such as E.I. DuPont, or it can prepared by the known Goldberg arylation reaction; and processes for the preparation of arylamines, and more specifically, processes for the preparation of N,N-bis(3,4- dimethylphenyl)-4-biphenylamines, which comprises the reaction of bis(3,4-dimethylphenyl)amine with a dialkyl, preferably dimethyl, iodobenzene, and which reaction is accomplished in the presence of a ligated copper II catalyst, and wherein the ligand is selected from the group consisting of monodentate tertiary amines and bidentate tertiary amines. The bis(3,4-dimethylphenyl)amine reactant is preferably prepared by the reaction of a dialkylbenzene, preferably 4-iodo-o-xylene, with a dialkyl, preferably 3,4-dimethyl benzene acetamide. The reactions can be accomplished at low temperatures, for example from about 100° C. (Centigrade) to about 150° C., preferably from about 120° C. to about 140° C., and more preferably at about 125° C., and wherein the catalyst is 1,10-phenanthrolato copper (II) chloride, dipyridino copper (II) chloride, 1,10-phenanthrolato copper (II) bromide, dipyridino copper (II) bromide, and more preferably 1,10-phenanthrolato copper (II) acetate. The catalyst selected is of importance and in embodiments is comprised of a copper containing organic ligand, and wherein the ligand is selected from the group consisting of monodentate tertiary amines and bidentate tertiary amines as indicated herein, and more specifically, copper catalysts or compounds, such as (1,10-phenanthrolato)Cu(X)$_2$ and bis(pyridinato)Cu(X)$_2$, wherein X is a halide, such as chloride or more preferably acetate. Ligation of the copper salt dramatically increases catalyst efficiency permitting very fast reactions to occur, generally over about several hours, at lower temperatures.

The important catalyst selected for the processes of the present invention is as illustrated herein, and in embodiments is comprised of ligated copper (II) salts, including the halide salts, such as chloride, bromide, and iodide, and more preferably acetate, and wherein the ligands are monodentate tertiary amines, or bidentate tertiary amines, such as 1,10-phenanthroline or pyridine. The amount of catalyst selected can vary, and generally, the catalyst is employed in effective amounts, such as from about 1 to about 20 mole percent of the reactants, and preferably from about 5 to about 12 mole percent of the limiting reactant. Examples of postulated formula structures for the ligand copper catalysts are as follows

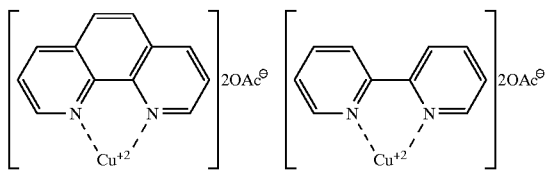

and in embodiments wherein the catalyst is 1,10-phenanthrolato copper (II) chloride, dipyridino copper (II) chloride, 1,10-phenanthrolato copper (II) bromide, or dipyridino copper (II) bromide, and most preferably 1,10-phenanthrolato copper (II) acetate and dipyridino copper (II) acetate.

The catalysts can be prepared as illustrated herein, and more specifically, by the reaction of a copper salt like a halide, such as cupric chloride, with the appropriate ligand like 1,10-phenanthroline, and which reaction is accomplished simply by mixing and stirring at room temperature. The reaction mixture is cooled and the product catalyst may, it is believed, be isolated by, for example, filtration. Preferably, the catalyst is prepared, or generated in situ.

In embodiments, the present invention relates to processes for the preparation of arylamines, and more specifically, a process for the preparation of N,N-bis(3,4-dimethylphenyl)-4-biphenylamine, which comprises the reaction of N,N-bis(3,4-dimethylphenyl)amine and an iodobiphenyl in the presence of a ligand copper catalyst, and wherein the ligand is selected from the group consisting of monodentate tertiary amines and bidentate tertiary amines, and which reaction is accomplished with heating at a temperature of, for example, preferably from about 120° C. to about 150° C.; wherein the iodobiphenyl is 4-iodobiphenyl; wherein subsequent to heating cooling is accomplished, and the N,N-bis(3,4-dimethylphenyl)-4-biphenylamine product is isolated; wherein the temperature is from about 120° C. to about 140° C.; wherein the temperature is about 125° C.; wherein from about 0.01 to about 0.1 molar equivalents of the ligated copper catalyst are selected, and the amount of bis(3,4-dimethylphenyl)amine is from about 0.95 to about 1.1 molar equivalents and the amount of iodobiphenyl is 1 molar equivalent; wherein the reaction is accomplished in the presence of 300 to 400 milliliters of an inert hydrocarbon solvent of, for example, toluene or xylene; wherein the catalyst is selected from the group consisting of 1,10-phenanthrolato copper (II) chloride, dipyridino copper (II) chloride, 1,10-phenanthrolato copper (II) bromide, dipyridino copper (II) bromide, and more preferably 1,10-phenanthrolato copper (II) acetate or dipyridino copper (II) acetate; a process for the preparation of N,N-bis(3,4-dimethylphenyl)-4-biphenylamine, which comprises the reaction of N,N-bis(3,4-dimethylphenyl) amine and an iodobiphenyl in the presence of a ligand copper catalyst, and wherein the ligand is selected from the group consisting of monodentate tertiary amines and bidentate tertiary amines; and to a process for the preparation of N,N-bis(3,4-dimethylphenyl)-4-biphenylamine, which comprises the reaction of N,N-bis(3,4-dimethylphenyl)amine and an iodobiphenyl in the presence of a ligand copper catalyst, and wherein the ligand is selected from the group consisting of monodentate tertiary amines and bidentate tertiary amines, and which reaction is accomplished at a temperature of from about 120° C. to about 150° C.; wherein the iodobiphenyl is 4-iodobiphenyl; wherein subsequent to heating cooling is accomplished, and the N,N-bis(3,4-dimethylphenyl)-4-biphenylamine product is isolated in high yields and excellent purity; wherein the temperature is from about 120° C. to about 140° C.; wherein the temperature is about 125° C.; wherein from about 0.01 to about 0.1 molar equivalents of the ligated copper catalyst are selected, the amount of bis(3,4-dimethylphenyl)amine selected is from about 0.95 to about 1.1 molar equivalents, and the amount of iodobiphenyl selected is about 1 molar equivalent; wherein the reaction is accomplished in the presence of a hydrocarbon solvent like an organic solvent of toluene or xylene; wherein the copper is copper (II); wherein the ligand is selected from the group consisting of 1,10-phenanthrolinepyridine and pyridine; wherein the N,N-bis(3,4-dimethylphenyl)amine is of the formula

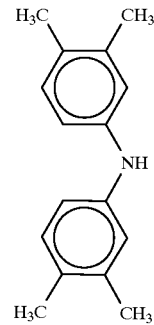

wherein the N,N-bis(3,4-dimethylphenyl)-4-biphenylamine product is of the formula

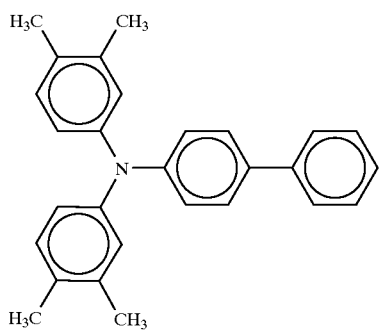

wherein the iodobiphenyl is of the formula

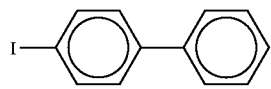

wherein the temperature is from about 10° C. to about 150° C.; wherein subsequent to heating cooling is accomplished, and the N,N-bis(3,4-dimethylphenyl)-4-biphenylamine product is isolated; a process for the preparation of N,N-bis (3,4-dimethylphenyl)-4-biphenylamine, which comprises the reaction of bis(3,4-dimethylphenyl)amine and 4-iodobiphenyl in the presence of a ligand copper catalyst, and wherein the ligand is selected from the group consisting of monodentate tertiary amines and bidentate tertiary amines, and which reaction is accomplished at an effective temperature, followed by cooling and isolating the N,N-bis (3,4-dimethylphenyl)-4-biphenylamine product; a process wherein the temperature is from about 120 to about 130° C.; a process wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate or dipyridino copper (II) acetate; a process wherein the catalyst is of the alternative formulas

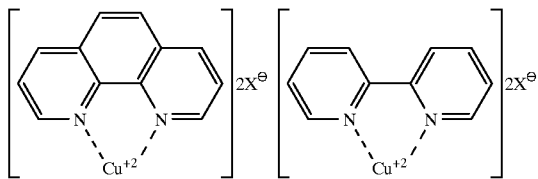

wherein X is a halide, such as chloride, bromide, iodide, or fluoride, or preferably is acetate; a process for the preparation of N,N-bis(3,4-dimethylphenyl)-4-biphenylamine by the reaction of N,N-bis(3,4-dimethylphenyl)amine and an iodobiphenyl in the presence of a ligand copper catalyst, and wherein the ligand is selected from the group consisting of monodentate tertiary amines and bidentate tertiary amines.

One embodiment of the present invention comprises the synthesis of N,N-bis(3,4-dimethylphenyl)-4-biphenylamine as follows. In an appropriate reaction flask equipped for mechanical stirring and fitted with an inert gas purge and Dean-Stark trap under a reflux condenser is placed in the following order: about 0.05 mole 4-iodobiphenyl, from about 0.45 to about 0.06 mole, and preferably 0.55 mole of N,N-bis(3,4-dimethylphenyl)amine, from about 0.001 to about 0.005, and preferably 0.0025 mole of cupric or copper (II) acetate monohydrate, from about 0.001 to about 0.005, and preferably 0.0025 mole of 1,10-phenanthroline, from about 0.3 to about 0.6, and preferably about 0.4 mole of flake potassium hydroxide and about 20 milliliters of toluene solvent. The reaction mixture is heated rapidly to reflux and kept at 120° C. until chromatographic analysis reveals the reaction to have reached completion. The water of reaction is collected by azeotropic distillation. Typically, 3 to 4 hours are required to complete the reaction. After cooling to room temperature, the reaction mixture is partitioned between about 200 milliliters of toluene and 150 milliliters of deionized water. The resulting layers are separated and the organic phase dried by azeotropic distillation of water. The toluene solution is then treated with about 10 grams of FILTROL-24™, an acid washed clay, and about 10 grams of Alcoa CG-20 alumina to primarily remove color. The toluene solution is filtered and the product may be recovered by evaporation of the solvent, and recrystallization of the product. The product, which can be identified by analytical methods, such as high performance liquid chromatography, possessed a high purity in embodiments as indicated herein and, more specifically, from about 97 to about 99 percent pure as determined by HPLC, that is high performance liquid chromography.

Numerous different layered photoresponsive imaging members containing the charge transporting amines generated with the process of the present invention can be provided. In embodiments, thus the layered photoresponsive imaging members are comprised of a supporting substrate, a charge transport layer, especially an arylamine hole transport component obtained with the process of the present invention, and situated therebetween a photogenerator layer comprised, for example, of phthalocyanines, hydroxygallium phthalocyanines, especially Type V, titanyl phthalocyanines, perylenes, especially BZP, selenium, especially trigonal selenium, selenium alloys, and the like, including other effective known photogenerating pigments. Also disclosed are positively charged layered photoresponsive, or photoconductive imaging members comprised of a supporting substrate, a charge transport layer, especially an arylamine hole transport layer, and as a top overcoating a photogenerating layer. Moreover, there can be provided negatively charged photoresponsive imaging members comprised of a supporting substrate, a thin adhesive layer, a photogenerator layer dispersed in a polymeric resinous binder, and as a top layer arylamine hole transporting molecules dispersed in a polymeric resinous binder, and which arylamine molecules are obtained with the processes of the present invention.

The imaging members can be prepared by a number of known methods, the process parameters, and the order of coating of the layers being dependent on the member desired. The imaging members suitable for positive charging can be prepared by reversing the order of deposition of photogenerator and hole transport layers. The photogenerating and charge transport layers of the imaging members can be coated as solutions or dispersions onto selective substrates by the use of a spray coater, dip coater, extrusion coater, roller coater, wire-bar coater, slot coater, doctor blade coater, gravure coater, and the like, and dried at from 40° C. to about 200° C. for from 10 minutes to several hours, and more specifically, about 5 hours under stationary conditions or in an air flow. The coating is accomplished to provide a final coating thickness of from 0.01 to about 30 microns after it has dried. The fabrication conditions for a given layer can be tailored to achieve optimum performance and cost in the final device. The imaging members are useful in xerographic imaging processes wherein, for example, when the pigment is a titanyl phthalocyanine, it absorbs light of a wavelength of from about 600 nanometers to about 900 nanometers. In these known processes, electrostatic latent images are initially formed on the imaging member, followed by development, and thereafter, transferring and fixing the image to a suitable substrate, such as paper. Moreover, the imaging members can be selected for electronic printing processes with gallium arsenide light emitting diode (LED) arrays which typically function at wavelengths of from about 660 to about 830 nanometers.

Substrate layers selected for the imaging members can be opaque or substantially transparent, and may comprise any suitable material having the requisite mechanical properties. Thus, the substrate may comprise apolyer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass, or the like. The substrate may be flexible, seamless, or rigid and many have a number of many different configurations, such as for example a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer may be of substantial thickness, for example over 3,000 microns, or of minimum thickness providing there are no adverse effects on the system. In one embodiment, the thickness of this layer is from about 75 microns to about 300 microns.

Generally, the thickness of the photogenerator layer depends on a number of factors, including the thicknesses of the other layers and the amount of photogenerator material contained in this layer. Accordingly, this layer can be of a thickness of from about 0.05 micron to about 10 microns when the photogenerator composition layer is present in an amount of from about 5 percent to about 100 percent by volume. In one embodiment, this layer is of a thickness of from about 0.25 micron to about 1 micron when the photogenerator composition is present in this layer in an amount of 30 to 75 percent by volume. The maximum thickness of this layer in an embodiment is dependent primarily upon factors, such as photosensitivity, electrical properties and mechanical considerations. The charge generator layer can be obtained by dispersion coating the photogenerating pigment, and a binder resin with a suitable solvent. The binder may be omitted. The dispersion can be prepared by mixing and/or milling the photogenerating pigment in equipment such as paint shakers, ball mills, sand mills and attritors. Common grinding media, such as glass beads, steel balls or ceramic beads, may be used in this equipment. The binder resin may be selected from a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. The solvents to dissolve these binders or resins depend upon the particular resin. In embodiments, it is desirable to select solvents that do not effect the other coated layers of the device. Examples of useful solvents are ketones, alcohols, aromatic hydrocarbons, halogenated aliphatic hydrocarbons, ethers, amines, amides, esters, and the like. Specific solvent examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethylformamide, dimethylacetamide, butyl acetate, ethyl acetate, methoxyethyl acetate, and the like.

The coating of the photogenerating pigment dispersion can be accomplished with spray, dip or wire-bar methods such that the final dry thickness of the charge generator layer is from about 0.01 to about 30 microns and preferably from about 0.1 to about 15 microns after being dried at from about 40° C. to about 150° C. for from about 5 to about 90 minutes.

Illustrative examples of polymeric binder resinous materials that can be selected for the photogenerator pigment include those polymers as disclosed in U.S. Pat. No. 3,121,006, the disclosure of which is totally incorporated herein by reference.

As adhesives usually in contact with the supporting substrate, there can be selected various known substances inclusive of polyesters, polyamides, poly(vinyl butyral), poly(vinyl alcohol), polyurethane and polyacrylonitrile. This layer is of a thickness of from about 0.05 micron to about 1 micron. Optionally, this layer may contain conductive and nonconductive particles, such as zinc oxide, titanium dioxide, silicon nitride, carbon black, and the like, to provide, for example, in embodiments of the present invention desirable electrical and optical properties.

Examples of the highly insulating and transparent resinous material or inactive binders selected for the charge transport layer include binders, such as those described in U.S. Pat. No. 3,121,006, the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000, with a molecular weight of from about 50,000 to about 100,000 being particularly preferred. Generally, the resinous binder contains from about 10 to about 75 percent by weight of the active charge transport material, and preferably from about 35 percent to about 50 percent of this material.

Methods of imaging and printing with the photoconductive members, or photoconductive imaging members illustrated herein, generally involve the formation of an electrostatic latent image on the imaging member, followed by developing the image with a toner composition, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The following Examples are being provided to further define various species of the present invention, it being noted that these Examples are intended to illustrate and not limit the scope of the present invention. Parts and percentages are by weight unless otherwise indicated. Yield and purity were determined by known analytical methods.

EXAMPLE I

Synthesis of N,N-bis(3,4-dimethylphenyl)-4-biphenylamine

In a 500 milliliter round bottomed flask equipped with mechanical stirrer and fitted with a Dean-Stark trap under a reflux condenser were placed 12.39 grams (0.055 mole) of bis(3,4-dimethylphenyl)amine, 14 grams (0.050 mole) of 4-iodobiphenyl, 0.50 gram (0.0025 mole) of cupric (copper II) acetate monohydrate, 0.45 gram (0,0025 mole) of 1,10-phenanthroline, 22.44 grams (0.4 mole) of flake potassium hydroxide and 20 milliliters of toluene solvent. The reaction was heated quickly to a reflux temperature of 120° C. and maintained at this temperature for 4 hours after which time chromatographic analysis revealed the reaction to be complete. The reaction was cooled to room temperature, about 25° C., and partitioned between 200 milliliters of toluene and 150 milliliters of deionized water. The resulting organic layer was separated and water removed by azeotropic distillation of the solvent under a Dean-Stark trap. The product was decolorized by slurry treating the toluene solution with 10 grams of FILTROL-24™, an acid washed clay, and 10 grams of Alcoa CG-20 alumina. After 3 hours stirring at reflux, the solution was hot filtered to remove the clay and alumina, and cooled to room temperature. Evaporation of the solvent and recrystallization from octane provided the above product compound in a yield of 10.2 grams (76 percent) and which product melted at 113.8° C. This product of N,N-bis(3,4-dimethylphenyl)-4-biphenylamine was suitable for further purification by conventional means to afford electronic grade, about 99 percent pure, product. The above total reaction time was an accelerated 4 hours.

The above synthesis, it is believed, can be repeated with different copper (II) ligand catalysts, at slightly higher or lower temperature, with different amounts of reactants with substantially similar results, and wherein the product purity thereof will be high, it is believed, for example 95 to 99 percent.

Other modifications of the present invention may occur to those skilled in the art subsequent to a review of the present application, and these modifications, including equivalents thereof, are intended to be included within the scope of the present invention.

What is claimed is:

1. A process for the preparation of N,N-bis(3,4-dimethylphenyl)-4-biphenylamine which comprises the reaction of N,N-bis(3,4-dimethylphenyl)amine and an iodobiphenyl in the presence of a ligand copper catalyst, wherein copper is of a valence of two and wherein the ligand is selected from the group consisting of monodentate tertiary amines and bidentate tertiary amines.

2. A process in accordance with claim 1 wherein the reaction is accomplished by heating.

3. A process in accordance with claim 2 wherein subsequent to heating, cooling is accomplished, and the N,N-bis(3,4-dimethylphenyl)-4-biphenylamine product is isolated, and wherein the iodobiphenyl is 4-iodobiphenyl.

4. A process in accordance with claim 2 wherein the temperature is from about 100° C. to about 150° C.

5. A process in accordance with claim 2 wherein the temperature is about 105° C. to about 150° C.

6. A process in accordance with claim 1 wherein from about 0.01 to about 0.1 molar equivalents of the ligated copper catalyst are selected, the amount of bis(3,4-dimethylphenyl)amine selected is from about 0.95 to about 1.1 molar equivalents, and the amount of iodobiphenyl selected is about 1 molar equivalent.

7. A process in accordance with claim 1 wherein the reaction is accomplished in the presence of a hydrocarbon solvent of toluene or xylene.

8. A process in accordance with claim 1 wherein the copper is copper (II).

9. A process in accordance with claim 1 wherein said ligand is selected from the group consisting of 1,10-phenanthrolinepyridine and pyridine.

10. A process in accordance with claim 2 wherein the N,N-bis(3,4-dimethylphenyl)amine is of the formula

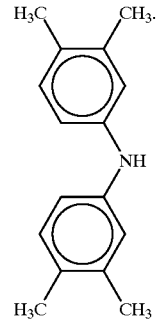

11. A process in accordance with claim 2 wherein the N,N-bis(3,4-dimethylphenyl)-4-biphenylamine product is of the formula

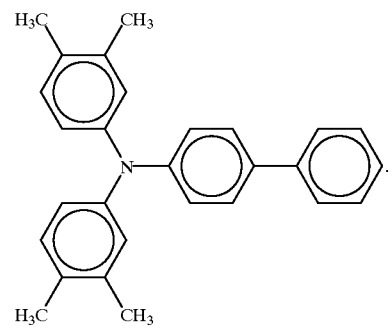

12. A process in accordance with claim 2 wherein the iodobiphenyl is of the formula

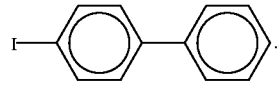

13. A process in accordance with claim 2 wherein subsequent to heating, cooling is accomplished, and the N,N-bis(3,4-dimethylphenyl)-4-biphenylamine product is isolated.

14. A process for the preparation of N,N-bis(3,4-dimethylphenyl)-4-biphenylamine which comprises the reaction of N,N bis(3,4-dimethylphenyl)amine and 4-iodobiphenyl in the presence of a ligand copper (II) catalyst, and wherein the ligand is selected from the group consisting of monodentate tertiary amines and bidentate tertiary amines, and which reaction is accomplished at a temperature of from about 120° C. to about 150° C., followed by cooling and isolating the N,N-bis(3,4-dimethylphenyl)-4-biphenylamine product.

15. A process in accordance with claim 14 wherein the temperature is from about 120° C. to about 130° C.

16. A process in accordance with claim 1 wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate.

17. A process in accordance with claim 2 wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate or dipyridino copper (II) acetate.

18. A process in accordance with claim 14 wherein the catalyst is selected from the group consisting of 1,10-phenanthrolato copper (II) chloride, dipyridino copper (II) chloride, 1,10-phenanthrolato copper (II) bromide, dipyridino copper (II) bromide, and 1,10-phenanthrolato copper (II) acetate or dipyridino copper (II) acetate.

19. A process in accordance with claim 1 wherein said catalyst is represented alternatively as follows

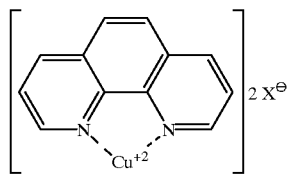

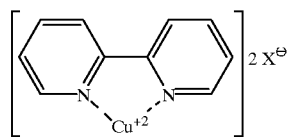

wherein X is a halide or acetate.

20. A process in accordance with claim 6 wherein said catalyst is of the alternative formulas

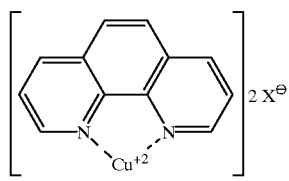

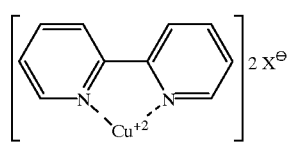

wherein X is a halide or acetate.

21. A process in accordance with claim 14 wherein said catalyst is of the alternative formulas

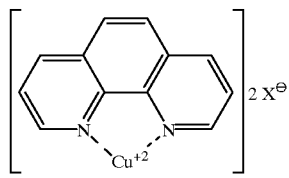

-continued

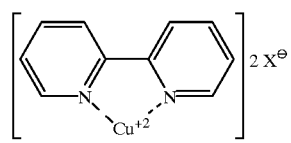

wherein X is a halide or acetate.

22. A process in accordance with claim 19 wherein X is acetate.

23. A process in accordance with claim 19 wherein X is chloride.

24. A process for the preparation of an arylamine which comprises the reaction of an arylamine and an iodobiphenyl in the presence of a ligand copper (II) catalyst.

25. A process in accordance with claim 24 wherein said catalyst is of the alternative formulas

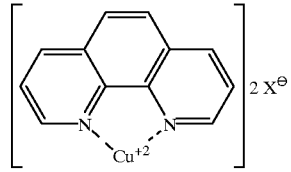

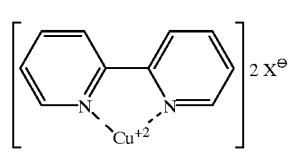

wherein X is an acetate, or halide.

26. A process in accordance with claim 2 wherein heating is accomplished at about 105° C.

27. A process for the preparation of N,N-bis(3,4-dimethylphenyl)-4-biphenylamine consisting essentially of the reaction of N,N-bis(3,4-dimethylphenyl)amine and an iodobiphenyl in the presence of a ligand copper catalyst, wherein copper is of a valence of two, and wherein the ligand is selected from the group consisting of monodentate tertiary amines and bidentate tertiary amines.

* * * * *